United States Patent [19]

Jouannetaud et al.

[11] 4,453,024

[45] Jun. 5, 1984

[54] PROCESS FOR THE META-HYDROXYLATION OF ALKYLPHENOLS AND THE ETHERS THEREOF IN A SUPERACIDIC MEDIUM

[75] Inventors: Marie-Paule Jouannetaud; Jean-Pierre Gesson; Jean-Claude Jacquesy, all of Poitiers, France

[73] Assignee: PCUK Produits Chimiques Ugine Kuhlmann, Courbevoie, France

[21] Appl. No.: 428,673

[22] Filed: Sep. 30, 1982

Related U.S. Application Data

[63] Continuation of Ser. No. 267,358, May 26, 1981.

[30] Foreign Application Priority Data

Jun. 3, 1980 [FR] France ................................ 80 12261

[51] Int. Cl.$^3$ ............................................. C07C 37/60
[52] U.S. Cl. .................................... 568/768; 568/771
[58] Field of Search ................................ 568/768, 771

[56] References Cited

U.S. PATENT DOCUMENTS

| 4,045,496 | 8/1977 | Seifert et al. | 568/771 |
| 4,223,165 | 9/1980 | Joufrett | 568/771 |
| 4,339,613 | 7/1982 | Olah | 568/768 |

FOREIGN PATENT DOCUMENTS

| 41441 | 12/1981 | European Pat. Off. | 568/771 |
| 2404114 | 8/1974 | Fed. Rep. of Germany | 568/803 |
| 50-151832 | 12/1975 | Japan | 568/771 |

OTHER PUBLICATIONS

Olah, "Science" Reprint Series 5, Oct. 1979, vol. 206, pp. 13–30.

*Primary Examiner*—Werren B. Lone
*Attorney, Agent, or Firm*—Pennie & Edmonds

[57] ABSTRACT

Process for hydroxylating alkylphenols in which the carbon atoms of the alkyl group bonded to the aromatic nucleus has at least one hydrogen atom bonded thereto and the phenolic ethers thereof, at the meta position relative to the phenol or ether function, by reacting the phenol compound with an aqueous hydrogen peroxide solution in the presence of a liquid superacid at low temperature.

6 Claims, No Drawings

PROCESS FOR THE META-HYDROXYLATION OF ALKYLPHENOLS AND THE ETHERS THEREOF IN A SUPERACIDIC MEDIUM

This is a continuation of application Ser. No. 267,358, filed May 26, 1981.

TECHNICAL FIELD

This invention relates to a process for the hydroxylation, with hydrogen peroxide, of alkylphenols and the ethers thereof in the meta position relative to the phenol or phenol ether function.

BACKGROUND ART

The known processes for the direct radical hydroxylation of phenol by means of the FENTON reagent (hydrogen peroxide+ferrous ions) result essentially in mixtures of pyrocatechol and hydroquinone, i.e., the hydroxylation preferentially occurs in the ortho and para positions of the phenol function. Only very small quantities of resorcinol are formed (hydroxylation in the meta position). Similarly, the photolysis of aqueous hydrogen peroxide solutions in the presence of paracresol at pH=3-8 mainly yields 4-methyl-pyrocatechol (3,4-dihydroxy-1-methyl-benzene). Processes of this kind are described, for example, in the work "Methoden der Organischen Chemie" (HOUBEN-WEYL), fourth edition, 6/1c, pages 30 to 34.

The ionic hydroxylation of phenols using hydrogen peroxide and carboxylic acids in the presence of a strong inorganic acid has also been studied. As an intermediate product, an organic peracid is formed, which is a very powerful oxidizing agent and has a tendency to degrade the diphenols formed. This process also essentially yields derivatives dihydroxylated in the ortho and para positions and yields virtually no meta derivative.

Other processes for the ionic hydroxylation of phenol use strong inorganic acids as catalyst, resulting in the formation of peroxonium ions. These processes make it possible to modify the pyrocatechol/hydroquinone ratio to some extent, but do not lead to the formation of resorcinol (cf. for example, the article "Hydroquinone et Pyrocatéchine par Hydroxylation Directe du Phénol", Chimie-Actualités, Nov. 3, 1976, pages 47-49).

In anhydrous hydrofluoric acid as solvent, phenol is also hydroxylated by hydrogen peroxide into a mixture of hydroquinone and pyrocatechol (J. Org. Chem., 35, 4028, 1970).

Similarly, the ionic hydroxylation of paracresol gives 20% of methylhydroquinone and 41% of 4-methyl-pyrocatechol (HOUBEN-WEYL, loc. cit. page 34).

Tests on the hydroxylation of aromatic hydrocarbons with hydrogen peroxide in a superacidic medium have been reported by G. A. Olah and his collaborators ("Oxyfunctionalization of Hydrocarbons-8-Electrophilic Hydroxylation of Benzene, Alkylbenzenes and Halobenzenes with $H_2O_2$ in Superacids", J. Org. Chem., 43, 865, 1978). Thus, toluene results in a 67% yield of a mixture of cresols, with an o/m/p ratio of 71/6/23.

DISCLOSURE OF THE INVENTION

The invention relates to a process for the hydroxylation of alkylphenols and their phenolic ethers with hydrogen peroxide in the presence of a liquid superacidic medium at a temperature between about 0° and −80° C. The process results in the introduction of a new phenol function in the meta position relative to the phenol or ether function of the alkylphenol or alkylphenol ether being hydroxylated.

Thus, in the light of the prior art, it is totally unexpected that the applicants should have found that alkylphenols and their ethers can be preferentially hydroxylated at the meta position of the phenol or ether function using hydrogen peroxide in a liquid superacid medium, at temperatures of from 0° to −80° C.

The presence of one or more alkyl substituents on the aromatic nucleus of the phenol or phenol ether is necessary for the satisfactory development of the reaction. Under the same hydroxylation conditions, ordinary phenol only produces a mixture of diphenols, consisting chiefly of hydroquinone and pyrocatechol; very little resorcinol is formed. Similarly, anisole produces a mixture of parahydroxyanisole and hydroquinone.

Various alkyl substituents can be carried by the aromatic nucleus of the phenol or phenol ether, such as methyl, ethyl, n-propyl, isopropyl, n-butyl or isobutyl radicals, etc., or cycloalkyl radicals, containing from 6 to 10 carbon atoms.

The alkyl radicals bonded to the aromatic nucleus by a tertiary carbon, such as tert.-butyl radicals, are excluded since, under the reaction conditions, the phenolic compounds substituted by these radicals undergo decomposition with displacement of the tert.-alkyl substituent in some cases. Thus, para-tert.-butylphenol leads to a mixture of phenol and hydroquinone, whereas 2,6-ditert.-butylphenol produces a mixture of phenol, hydroquinone and p-tert.-butylphenol. Thus, the alkyl radicals useful according to the invention can be defined as those containing at least one hydrogen atom on the carbon atom bonded to the aromatic nucleus.

Examples of liquid superacidic media in which the reaction takes place include superacids such as "magic acid" $FSO_3H\text{-}SbF_5$, fluoroantimonic acid $HF\text{-}SbF_5$, the complex of trifluoromethanesulphonic acid and antimony pentafluoride $CF_3SO_3H\text{-}SbF_5$, the complex of hydrofluoric acid and boron trifluoride $HF\text{-}BF_3$, etc. These acids have $H_o$ acidities, estimated on the HAMMETT logarithmic scale, of up to about −25, but the invention is not thereby limited. In contrast, the corresponding $H_o$ acidity values are −11 for 100% sulfuric acid, and −10 for 100% hydrofluoric acid. These liquid superacids thus have acidities up to $10^{14}$ times higher than those of conventional strong inorganic acids.

The hydrogen peroxide used in the process according to the invention is in the form of commercial aqueous solutions, in which the $H_2O_2$ content may range from 20 to 98% by weight. Superacids are, in effect, consumed by water and cease to act as superacids in aqueous solution. Therefore, the amount of superacid added to the reaction mixture will depend on the amount of water contained therein or the water content in the $H_2O_2$ aqueous solutions being employed. A sufficient excess of superacid over that consumable by the water in the reaction medium should thus be used to insure superacidity or a superacid medium. The proportion of superacid in relation to the alkylphenol or phenol ether which is to be hydroxylated may vary within wide limits. It is only necessary to provide a superacid reaction medium, but it is preferred to use about 2 moles of superacid per mol of phenol or phenol ether under anhydrous conditions or in excess of that consumable by the water. Thus, if a 30% $H_2O_2$ solution is used and this amount of water consumes 15 moles of the superacid, 17 mols of the superacid should be employed. The reaction proceeds quite nicely using 2 mols of the superacid as the superacidity medium, and although considerably more superacid could be used, it is not practical or economical to do so. It is thus obvious that savings in superacid can be accomplished by reduction in the water content of the $H_2O_2$ solution employed. The process is preferably carried out with an excess of hydrogen peroxide in relation to the stoichiometric amount.

The hydroxylation reaction according to the invention is rapid and usually lasts from a few minutes to half an hour. In general, it produces the desired meta-hydroxylated derivative in good yields without significant side reactions. However, in the case of phenol ethers wherein the phenol function is substituted by an ethyl group, it sometimes happens that the ether function is split, with regeneration of the phenol function. Under certain conditions, the radical detached from the ether function may alkylate the aromatic nucleus, occasionally while being isomerized. Thus, p-cresol-ethyl ether gives 2-methyl-3-ethylresorcinol and p-cresol-n-propyl ether gives 2-methyl-3-isopropyl-resorcinol. Occasionally, small quantities of a tris-hydroxylated derivative in the meta position may also be obtained.

The procedure used to implement the process according to the invention and which is used in the following Examples, is very simple.

The liquid superacid, the aqueous hydrogen peroxide solution and the phenol or phenol ether to be hydroxylated are successively placed in a poly(tetrafluoroethylene) container which has been cooled to the desired temperature and is fitted with a magnetic stirrer. The homogenized mixture is kept at the desired temperature for the required time, then poured onto a mixture of water, ice and acidic sodium carbonate. After neutralization, the solution is extracted three times with ether. The ethereal phase is washed with water until neutral, then dried over anhydrous sodium sulphate. After evaporation of the ether, the crude reaction product is filtered over silica gel and analyzed by chromatography in the vapor phase.

When the complex $HF\text{-}SbF_5$ is used as the superacid, it is diluted with an equivalent volume of anhydrous hydrofluoric acid. For example, 1.7 cm$^3$ of hydrofluoric acid and 1.7 cm$^3$ of $HF\text{-}SbF_5$ complex are used per millimol of phenol or phenol ether. When hydroxylation is carried out with 95% by weight hydrogen peroxide, 1.4 equivalents of $H_2O_2$ are used for the phenols (reaction time 30 minutes at $-41°$ C.) and 1.2 equivalents of $H_2O_2$ for the phenol ethers (reaction time 5 minutes at $-41°$ C.). If a 30% by weight aqueous solution of hydrogen peroxide is used for the hydroxylation, the same equivalents of $H_2O_2$ are used as before, but the molar ratio of $HF\text{-}SbF_5$ to phenol is altered to 16–17. The reaction times are again 30 minutes at $-41°$ C. for phenols and 5 minutes at $-41°$ C. for phenol ethers.

The $HF\text{-}BF_3$ complex is formed by bubbling a current of boron trifluoride into anhydrous hydrofluoric acid at $-41°$ C. until saturation point, over a period of about 5 minutes.

The $CF_3SO_3H\text{-}SbF_5$ complexes and the $FSO_3H\text{-}SbF_5$ complex are formed by mixing the required quantities of sulfonic acid and antimony pentafluoride together at $-41°$ C.

The following Table shows various Examples which illustrate the invention without restricting it. Examples 1 to 6 relate to various alkylphenols; Examples 7 to 15 relate to the various alkylphenol ethers. The procedure used in the following Examples is as outlined above. In Examples 1 to 8 and 11 to 15, a 95% hydrogen peroxide solution is used with a molar ratio of $HF\text{-}SbF_5$ to phenol or phenol ether of 6. In Examples 9 and 10 a 95% hydrogen peroxide is used with $CF_3SO_3H\text{-}SbF_5$ and $HF\text{-}BF_3$ molar ratios to phenol ether of 20.

TABLE I

| Example Number | Starting Product | Superacid Medium | Temperature °C. | Conversion Rate % | Reaction Products |
|---|---|---|---|---|---|
| 1 | p-cresol | HF—SbF$_5$ | −41 | 78 | 4-methyl-resorcinol |
| 2 | 2,4-dimethyl-phenol | HF—SbF$_5$ | −41 | 90 | 4,6-dimethyl-resorcinol (58%) 2,4-dimethyl-resorcinol (32%) |
| 3 | 3,4-dimethyl-phenol | HF—SbF$_5$ | −41 | 88 | 4,5-dimethyl-resorcinol |
| 4 | 2,6-dimethyl-phenol | HF—SbF$_5$ | −41 | <30 | 2,4-dimethyl-resorcinol (a few %) 2,4-dimethyl-phloroglucinol (4%) |
| 5 | ortho-cresol | HF—SbF$_5$ | −40 | 28 | methyl-hydroquinone (16.8%) 4-methyl-resorcinol (3.9%) 3-methyl-pyrocatechol (4.2%) 2-methyl-resorcinol (3.1%) |
| 6 | 4-methyl-3-ethyl-phenol | HF—SbF$_5$ | −40 | 57 | 2-methyl-3-ethyl-resorcinol |
| 7 | 4-methyl-anisole | HF—SbF$_5$ | −41 | 75 | 3-hydroxy-4-methyl-anisole |
| 8 | 4-methyl-anisole | HF—SbF$_5$ | 0 | 75 | 3-hydroxy-4-methyl-anisole |
| 9 | 4-methyl-anisole | CF$_3$SO$_3$H—SbF$_5$ | −41 | 75 | 3-hydroxy-4-methyl-anisole |
| 10 | 4-methyl-anisole | HF—BF$_3$ | −41 | 52 | para-cresol (26%) 2-hydroxy-4-methyl-anisole (10%) 3-hydroxy-4-methyl-anisole (16%) |
| 11 | 2,4-dimethyl-anisole | HF—SbF$_5$ | −41 | 84 | 5-hydroxy-2,4-dimethyl-anisole |
| 12 | 3,4-dimethyl-anisole | HF—SbF$_5$ | −41 | 75 | 5-hydroxy-3,4-dimethyl-anisole |
| 13 | 2,6-dimethyl-anisole | HF—SbF$_5$ | −41 | 85 | 3-hydroxy-2,6-dimethyl-anisole (55%) 2,4-dimethyl-resorcinol (22%) 3,5-dihydroxy-2,6-dimethyl-anisole (8%) |
| 14 | ethyl ether of p-cresol | HF—SbF$_5$ | −41 | 68 | 4-methyl-5-ethyl-resorcinol |
| 15 | n-propyl ether of p-cresol | HF—SbF$_5$ | −41 | 50 | 4-methyl-5-isopropyl-resorcinol |

We claim:

1. A process for hydroxylating mono-phenols having one or more $C_1$ to $C_8$ alkyl substituents in which the carbon atom of the alkyl group bonded to the aromatic nucleus has at least one hydrogen atom bonded thereto and the phenolic ethers thereof in the meta position relative to the phenol or ether function which comprises reacting the phenol with an aqueous solution of hydrogen peroxide in the presence of a liquid superacid having a $H_0$ acidity estimated on the HAMMETT logarithmic scale of greater than $-11$ up to about $-25$ at a temperature of between 0° and $-80°$ C.

2. The process according to claim 1 in which the liquid superacid is the complex $HF\text{-}SbF_5$.

3. The process according to claim 1 in which the liquid superacid is the complex $CF_3SO_3H\text{-}SbF_5$.

4. The process according to claim 1 in which the liquid superacid is the complex $HF\text{-}BF_3$.

5. The process according to any one of claims 1 to 4 in which the starting phenol or phenol ether has, on the aromatic nucleus, 1 to 4 alkyl or cycloalkyl substituents, containing from 1 to 10 carbon atoms and arranged so as to leave at least one meta position free relative to the phenol or ether function.

6. The process accoring to any one of claims 1 to 5 in which the starting phenol ether has on the ether function an alkyl or cycloalkyl radical containing from 1 to 10 carbon atoms.

* * * * *

UNITED STATES PATENT AND TRADEMARK OFFICE
CERTIFICATE OF CORRECTION

PATENT NO. : 4,453,024
DATED : June 5, 1984
INVENTOR(S) : Marie-Paule Jouannetaud et al.

It is certified that error appears in the above—identified patent and that said Letters Patent is hereby corrected as shown below:

Column 4, line 7, reads "$HF-SbF_3$", should read --$HF-SbF_5$--.

Signed and Sealed this

Thirtieth Day of October 1984

[SEAL]

Attest:

Attesting Officer

GERALD J. MOSSINGHOFF
Commissioner of Patents and Trademarks